US010835139B2

(12) United States Patent
Rappel et al.

(10) Patent No.: US 10,835,139 B2
(45) Date of Patent: Nov. 17, 2020

(54) METHOD TO DETERMINE WAVEFRONT VECTOR FLOW-FIELD AND VORTICITY FROM SPATIALLY-DISTRIBUTED RECORDINGS

(71) Applicant: THE REGENTS OF THE UNIVERSITY OF CALIFORNIA, Oakland, CA (US)

(72) Inventors: Wouter-Jan Rappel, San Diego, CA (US); David Vidmar, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 51 days.

(21) Appl. No.: 16/087,560

(22) PCT Filed: Mar. 24, 2017

(86) PCT No.: PCT/US2017/024142
§ 371 (c)(1),
(2) Date: Sep. 21, 2018

(87) PCT Pub. No.: WO2017/165846
PCT Pub. Date: Sep. 28, 2017

(65) Prior Publication Data
US 2019/0104958 A1    Apr. 11, 2019

Related U.S. Application Data

(60) Provisional application No. 62/312,866, filed on Mar. 24, 2016.

(51) Int. Cl.
*A61B 5/04*     (2006.01)
*A61B 5/00*     (2006.01)
(Continued)

(52) U.S. Cl.
CPC ........ *A61B 5/04011* (2013.01); *A61B 5/0422* (2013.01); *A61B 5/0452* (2013.01);
(Continued)

(58) Field of Classification Search
CPC . A61B 5/04011; A61B 5/6869; A61B 5/7278; A61B 5/0422; A61B 5/7207;
(Continued)

(56) References Cited

U.S. PATENT DOCUMENTS 8,521,266 B2    8/2013   Narayan et al.
8,700,140 B2    4/2014   Narayan et al.
(Continued)

OTHER PUBLICATIONS

Kalifa, J, et al. "Mechanisms of wave fractionation at boundaries of high-frequency excitation in the posterior left atrium of the isolated sheep heart during atrial fibrillation," Circulation, vol. 113, No. 5, Feb. 7, 2006, pp. 626-633.
(Continued)

*Primary Examiner* — Mallika D Fairchild
(74) *Attorney, Agent, or Firm* — Eleanor Musick; Musick Davison LLP (57) ABSTRACT

Methods and systems are provided for determination and mapping of vector fields which characterize wavefront motion through space and time. The inventive methods and systems utilize data from spatially-distributed locations and maps wavefront vector flow fields in an entirely automated manner. These maps can be used to characterize the activation as planar, centrifugal, or rotational. Further, the strength of rotation or divergence is determined from these fields and can be used to select spatial points of significantly increased rotational or focal activity. As applied to electrophysiological data recorded during heart rhythm disorders in patients, the inventive method provides a means of visual interpretation of complex activation maps. The information related to the strength and location of rotation and centrifugal
(Continued)

activity during episodes of arrhythmia can guide therapies designed to treat such disorders.

23 Claims, 6 Drawing Sheets (51) Int. Cl.
*A61B 5/0452* (2006.01)
*A61B 5/042* (2006.01)
*A61N 1/368* (2006.01)

(52) U.S. Cl.
CPC .......... *A61B 5/4836* (2013.01); *A61B 5/6869* (2013.01); *A61B 5/7207* (2013.01); *A61B 5/7278* (2013.01); *A61B 5/0006* (2013.01); *A61B 5/0022* (2013.01); *A61B 5/6858* (2013.01); *A61N 1/368* (2013.01)

(58) Field of Classification Search
CPC ... A61B 5/0452; A61B 5/4836; A61B 5/0022; A61B 5/6858; A61B 5/0006; A61N 1/368
See application file for complete search history.

(56) References Cited

U.S. PATENT DOCUMENTS

| | | | |
|---|---|---|---|
| 8,838,222 | B2 | 9/2014 | Narayan et al. |
| 8,838,223 | B2 | 9/2014 | Narayan et al. |
| 8,868,169 | B2 | 10/2014 | Narayan et al. |
| 9,089,269 | B2 | 7/2015 | Narayan et al. |
| 9,241,667 | B2 | 1/2016 | Narayan et al. |
| 9,375,156 | B2 | 6/2016 | Narayan et al. |
| 9,380,950 | B2 | 7/2016 | Narayan et al. |
| 9,439,573 | B2 | 9/2016 | Narayan et al. |
| 9,549,684 | B2 | 1/2017 | Narayan et al. |
| 9,717,436 | B2 | 8/2017 | Narayan et al. |
| 9,955,879 | B2 | 5/2018 | Narayan et al. |
| 10,092,196 | B2 | 10/2018 | Narayan et al. |
| 2001/0039443 | A1 | 11/2001 | Chen |
| 2002/0010392 | A1 | 1/2002 | Desai |
| 2003/0236466 | A1 | 12/2003 | Tarjan et al. |
| 2004/0059237 | A1 | 3/2004 | Narayan et al. |
| 2010/0156898 | A1 | 6/2010 | Voros et al. |
| 2010/0198283 | A1 | 8/2010 | Zhang et al. |
| 2012/0283590 | A1 | 11/2012 | Afonso |
| 2014/0371609 | A1 | 12/2014 | Narayan et al. |
| 2015/0065836 | A1 | 3/2015 | Thakur et al. |
| 2016/0007932 | A1 | 1/2016 | Laughner et al. |

OTHER PUBLICATIONS

Masse, S., et al., "Wave similarity of human ventricular fibrillation from bipolar electrograms", Eurospace (2007) vol. 9, pp. 10-19.

Nademanee, Koonlawee, et al., "A new approach for catheter ablation of atrial fibrillation: mapping of the electrophysiologic substrate", J. Amer.Coll.Cardiol., vol. 43, No. 11, Jun. 2, 2004, pp. 2044-2053.

Narayan, S.M. et al.; "Clinical Mapping Approach to Diagnose Electrical Rotors and Focal Impulse Sources for Human Atrial Fibrillation"; J. Cardiovasc Electrophysiol., May 2012, vol. 23(5), pp. 447-454.

Narayan, S.M. et al.; "Repolarization and Activation Restitution Near Human Pulmonary Veins and Atrial Fibrillation Initiation: Mechanisms Separating Persistent From Paroxysmal AF"; J. Am Coll Cardiol., Oct. 7, 2008, vol. 52(15), pp. 1222-1230.

PCT/US2017/024115 International Search Report and Written Opinion dated Jun. 6, 2017, 9 pages.

Sahadevan, J., K. Ryu, et al. "Epicardial Mapping of Chronic Atrial Fibrillation in Patients: Preliminary Observations." Circulation; 2004; vol. 110(21): p. 3293-3299.

Sanders, P., et al., "Spectral Analysis Identifies Sites of High-Frequency Activity Maintaining Atrial Fibrillation in Humans." Circulation, 2005, vol. 112(6): pp. 789-797.

Skanes, A. C. et al.; "Spatiotemporal Periodicity During Atrial Fibrillation in the Isolated Sheep Heart." Circulation, 1998, vol. 98(12): pp. 1236-1248.

Tabereaux P. B., et al.; "Activation patterns of Purkinje fibers during long-duration ventricular fibrillation in an isolated canine heart model." Circulation, 2007, vol. 116(10): pp. 1113-1119.

Vidmar D. et al., "Phase synchrony reveals organization in human atrial fibrillation", Am J Heart Circ Physiol, 2015, vol. 309; pp. H2118-H2126.

PCT/US2017/024142, International Search Report and Written Opinion, dated Jun. 19, 2017, 8 pages.

METHOD TO DETERMINE WAVEFRONT VECTOR FLOW-FIELD AND VORTICITY FROM SPATIALLY-DISTRIBUTED RECORDINGS

RELATED APPLICATIONS

This application is a 371 national stage filing of International Application No. PCT/US2017/024142, filed Mar. 24, 2017, which claims the benefit of the priority of U.S. Provisional Application No. 62/312,866, filed Mar. 24, 2016, each of which is incorporated herein by reference in its entirety.

GOVERNMENT RIGHTS

This invention was made with government support under Grant No. HL122384 awarded by the National Institutes of Health. The government has certain rights in the invention.

FIELD OF THE INVENTION

The present invention discloses a system and method for determination and mapping of vector fields characterizing wavefront motion through space and time. As applied to electrophysiological data recorded during heart rhythm disorders in patients, the method provides a means of visual interpretation of complex activation maps. The information related to the strength of rotation and divergence during episodes of arrhythmia can guide therapies designed to treat such disorders.

BACKGROUND

Heart rhythm disorders represent a class of medical ailments affecting millions of people worldwide, often leading to serious side-effects including heart-failure, stroke, and mortality. Two of the most common arrhythmias are ventricular fibrillation (VF) and atrial fibrillation (AF), whereby the coordinated contraction of the heart loses its regularity and begins to contract in an irregular, quivering manner. While there remain scientific questions regarding the exact mechanisms allowing these disordered episodes to persist, it is believed that rotational waves or focal sources of electrical activity play a key role.

Basket catheters, consisting of multiple spatially-distributed electrodes, can record the electrical activity occurring during episodes of arrhythmia in the form of clinical electrograms. The data from these electrograms can then be used to infer the underlying propagation of electrical waves which cause the contraction of the heart. Visual interpretation of phase maps, as inferred from the electrograms, often reveals spiral waves of activation (rotors) or focal sources during AF or VF. A promising therapy aimed at treating the underlying arrhythmic mechanism consists of ablating regions of tissue which appear, by manual visual examination, to correspond to the location of stable rotor cores or focal sources.

Identification of the appropriate target for ablation can be a challenge because current tools to identify and locate the cause of the heart rhythm disorder are less than optimal, limiting efforts to precisely deliver energy to the region needed to terminate and eliminate the disorder without collateral damage to otherwise healthy regions of the heart. For human AF, particularly persistent AF, the absence of identified and located causes means that ablation is empiric and often involves damage to approximately 30-40% of the atrium that could theoretically be avoided if the cause(s) were identified and located for minimally invasive ablation and/or surgical therapy (Cox 2005). In persistent AF, a highly prevalent form of AF, ablation has a single procedure success rate of only 50-60% (Cheema, Vasamreddy et al. 2006; Calkins, Brugada et al. 2007) despite lengthy 4-5 hour procedures and a 5-10% rate of serious complications (Ellis, Culler et al. 2009) including death (Cappato, Calkins et al. 2009).

Existing systems display data that the practitioner must still interpret based on experience—there is no widely-available tool to directly identify and locate the cause of the disorder to enable the practitioner to detect, diagnose and treat it. Such systems are based on currently used methods described in, for example, U.S. Pat. Nos. 5,662,108, 5,662,108, 6,978,168, 7,289,843 and others by Beatty and coworkers, U.S. Pat. No. 7,263,397 by Hauck and Schultz, U.S. Pat. No. 7,043,292 by Tarjan and coworkers, U.S. Pat. No. 6,892,091 and other patents by Ben-Haim and coworkers and U.S. Pat. No. 6,920,350 by Xue and coworkers. These methods and instruments detect, analyze and display electrical potentials, often in sophisticated 3-dimensional anatomic representations, but still fail to identify and locate the cause of heart rhythm disorders, particularly for complex disorders such as AF or VF. This is also true for patents by Rudy and coworkers (U.S. Pat. Nos. 6,975,900 and 7,016,719, among others), which use signals from the body surface to "project" potentials on the heart.

Certain known methods for identifying and locating causes for heart rhythm disorders may work in simple rhythm disorders, but are not useful for identifying causes of complex disorders such as AF, VF or polymorphic VT. Activation mapping (tracing activation back to the earliest site) is useful only for simple tachycardias, works poorly for atrial flutter (AFL, a continuous rhythm without a clear "start"), and not at all for AF with variable activation paths. Entrainment mapping uses pacing to identify sites where the stimulating electrode is at the cause of a rhythm, yet pacing cannot be applied in AF and even some "simple" rhythms such as atrial tachycardias due to automatic mechanisms. Stereotypical locations are known for the cause(s) of atrio-ventricular node reentry, typical AFL and patients with early (paroxysmal) AF, but not for the vast majority of patients with persistent AF (Calkins, Brugada et al. 2007), VF and other complex disorders.

Prior methods have largely focused on mapping of the anatomy to identify whether a patient has a heart disorder, rather than determining the cause or source of the disorder. Thus, there is an urgent need for methods and tools to directly identify and locate causes for heart rhythm disorders in individual patients to enable curative therapy. This is particularly critical for AF and other complex rhythm disorders for which, ideally, a system would detect localized causes for ablation by minimally invasive, surgical or other methods.

As described by Narayan and Rappel in U.S. Pat. Nos. 8,521,266, 8,838,222 and 8,838,223, each of which is incorporated herein by reference, computational methods for analyzing physiological signals generate activation patterns that can be used to identify sources of heart rhythm disorders. One approach for creating these "activation trails" includes phase mapping of signals obtained from multi-electrode sensors, including basket electrodes. Generation of phase maps involves assigning a phase co to the signal at every electrode and at every time point. The phase at the exact location of the tip of the rotor is undefined and summing up the gradient of the phase of neighboring sites results in a "phase jump" of $2\pi$. Thus, a rotor location corresponds to a phase singularity. Mathematically, these phase singularities can be found by evaluating a line integral over a closed curve as $\oint \vec{\nabla}\varphi \cdot d\vec{l} = \pm 2\pi$ where the line integral is taken over a path l surrounding the phase singularity. Since the signal from the electrode is a single observable, the determination of the phase requires special attention. A number of different methods can be employed depending on the quality of the electrode signal.

Determination and detection of rotors is currently subjective and particularly disposed to operator error in mismarking or missing rotor or focal activation. The current invention allows for a quantitative and automated process by which to detect regions of tissue likely to contain a rotor core or focal source, and allows for a quantification of the stability of a given rotor or focus. The invention also allows for visual guides to clarify propagation patterns during the complex phase maps recorded during arrhythmias. These methods are expected to provide substantial aid for ablation therapies targeting rotor and focal activity by minimizing erroneous visual interpretations of complicated phase maps.

BRIEF SUMMARY

According to exemplary embodiments, a system and method for determination and mapping of vector fields characterize wavefront motion through space and time. The inventive method utilizes data from spatially-distributed locations and maps wavefront vector flow fields in an entirely automated manner. These maps can be used to characterize the activation as planar, centrifugal, or rotational. Further, the strength of rotation or divergence is determined from these fields and can be used to select spatial points of significantly increased rotational or focal activity. As applied to electrophysiological data recorded during heart rhythm disorders in patients, the inventive method provides a means of visual interpretation of complex activation maps. The information related to the strength and location of rotation and centrifugal activity during episodes of arrhythmia can guide therapies designed to treat such disorders.

In one aspect of the invention, a method for analyzing complex cardiac activation patterns, comprises collecting, via a computer processor, a plurality of cardiac signals at a plurality of locations corresponding to spatial locations of a patient's heart; determining activation times within the cardiac signals; binning the activation times according to a selected bin size; coarse-graining the binned activation times to generate coarse-grained data; determining at least one wavefront flow field (WFF) for a plurality of time windows using the coarse-grained data; computing a local wavefront vorticity using the at least one WFF to determine rotational activity surrounding each spatial location; and generating a vorticity map indicating likely rotational sources of complex cardiac activations.

In another aspect of the invention, a system for analyzing complex cardiac activation patterns comprises a computer processor programmed to execute the steps of: collecting, via a computer processor, a plurality of cardiac signals at a plurality of locations corresponding to spatial locations of a patient's heart; determining activation times within the cardiac signals; binning the activation times according to a selected bin size; coarse-graining the binned activation times to generate coarse-grained data; determining at least one wavefront flow field (WFF) for a plurality of time windows using the coarse-grained data; computing a local wavefront vorticity using the at least one WFF to determine rotational activity surrounding each spatial location; and generating a vorticity map indicating likely rotational sources of complex cardiac activations.

DETAILED DESCRIPTION OF EMBODIMENTS OF THE INVENTION

In the embodiments described below, a quantitative and automated system and process is provided by which to detect regions of tissue likely to contain a rotor core or focal source, which also allows for a quantification of the stability of a given rotor. The system and methodology also provides for visual guides to clarify propagation patterns during the complex phase maps recorded during arrhythmias. These methods may provide substantial aid for ablation therapies targeting rotor and focal activity by minimizing erroneous visual interpretations of complicated phase maps.

Definitions

For purposes of this invention, the following definitions shall apply:

"Detecting/Diagnosing": The terms detecting and diagnosing a rhythm disorder are used interchangeably in this application.

"Activation time" means the time of activation onset for a given heart signal.

"Activation time duration" means the time period and the signal waveform between the times of activation onset and offset for the signal of a given heartbeat. Diastolic interval is the time period from activation offset of the prior beat to activation onset of the present beat.

"Activation trail" means the ordering of the activation time onset at the sensor locations to create a discernible signature pattern, for example, including without limitation a rotational pattern around a core region indicative of a rotor, a radially emanating pattern from a core region, indicative of a focal beat cause, or a dispersed pattern, requiring further signal sampling and repeating of above analysis steps.

"Identify and locate" means the process of discerning the presence of a localized or dispersed cause of the heart rhythm disorder, then locating said cause relative to sensor locations or relative to known anatomic positions in the heart.

"Heart rhythm disorder" means an abnormal rhythm, often requiring treatment. These include without limitation, rapid rhythms of the top chambers of the heart (atria) such as rapid and abnormal activation of the normal sinus node (inappropriate sinus tachycardia or sinus node reentry), atrial tachycardia (AT), supraventricular tachycardia (SVT), atrial flutter (AFL), premature atrial complexes/beats (PAC) and the complex rhythms of atrial fibrillation (AF) and certain forms of atypical atrial flutter. Rapid rhythms can also occur in the bottom chambers of the heart (ventricles), including such as ventricular tachycardia (VT), ventricular fibrillation (VF), torsades de pointes and premature ventricular complexes/beats (PVC). Heart rhythm disorders can also be slow, including sinus bradycardia, ectopic atrial bradycardia junctional bradycardia, atrioventricular block and idioventricular rhythm.

"Cause of biological or heart rhythm disorder", which is used interchangeably with "source of the biological or heart rhythm disorder" in this application, refers to, without limitation, a rotational pattern of activation sequence around a core region indicative of a rotor, a radially emanating pattern from a core region indicative of a focal beat cause, or a dispersed pattern. In this invention, when a dispersed cause is found, signal sampling is extended to additional multiple locations and the detection and analysis steps of the invention are repeated. These causes are directly responsible for the perpetuation of the heart rhythm disorder.

"Sensor", which is used interchangeably with "electrode", refers to an apparatus for detecting and transmitting signals from the heart or to the heart.

Exemplary Methodology

Figure 1:
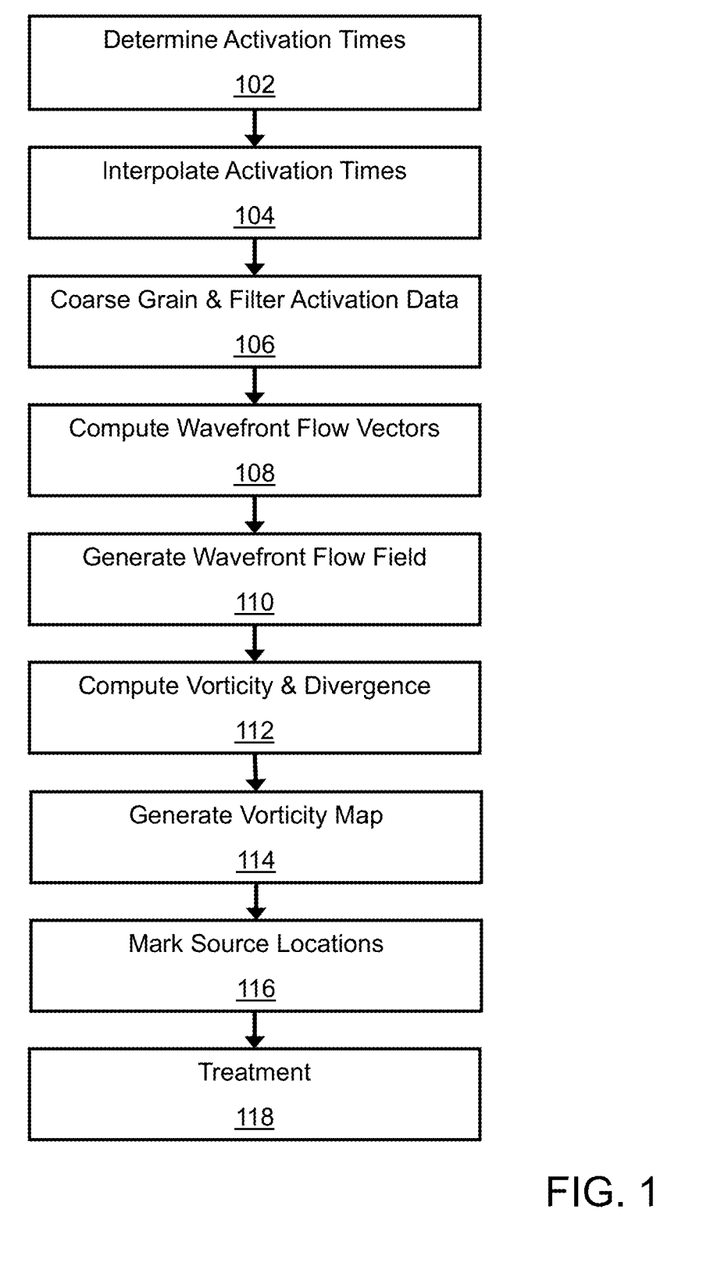
FIG. 1 is a schematic diagram illustrating an embodiment of the inventive method.

One embodiment of the exemplary methodology for determining and mapping vector flow fields is described below and illustrated by the schematic diagram in FIG. 1. In a first step 102, activation time recordings may be used, such as recordings from human patients which are derived from a recording grid. These activation times may be interpolated in step 104 onto a finer grid, for example by interpolating 2×2 squares of activation times across the computational domain. Or, the phase $\phi(t)$ of each recording site can be computed with time through linear interpolation such that the phase increases by 2*pi between each successive activation. Each site's phase can then be represented as a complex unit vector defined as $f(t)=\exp(i\phi(t))$. These complex unit vectors can be interpolated to a grid for all times, and the phase angle of these interpolated vectors with time can be computed from the inverse tangent: $\text{Angle}(f(t))=\tan^{-1}[\sin(\phi)(t))/\cos(\phi)(t)]$. Activation times are marked, on this interpolated grid, as points where the phase changes by $2\pi$.

If some temporal smoothing is desired, the complex unit vectors f(t) will also be temporally averaged to create smoother activation maps. This can be achieved by computing the average cycle length T of a given episode of fibrillation, and using that to define the average expected time evolution of phase for a given recording site. An "average" phase for a given recording site is then computed as the angle of the sum over some window of time of complex unit vectors, with each vector shifted to account for the expected temporal change of phase as determined by T. This time-averaged phase for a chosen time window $\tau$, therefore, is defined by the following equation:

$$\phi_\tau(t) \stackrel{def}{=} \text{Angle}\left(\sum_{t'=-\tau}^{+\tau} f(t+t')e^{-\frac{2\pi i t'}{T}}\right) \quad (1)$$

where the sum is over all data points within the 2 $\tau$ data window. Activation times can be determined from these interpolated phases as points where the phase changes $2\pi$.

In step 106, once activation times have been interpolated, time is binned with an appropriate bin size and the activation time data is coarse-grained by determining all recording sites which have activated for each time bin. We will call the coarse-grained activation data of the $i^{th}$ recording site $\varphi_i(t)$, such that $\varphi_i(t)=1$ if the recording site "i" has activated within the time bin corresponding to "t" and $\varphi_i(t)=0$ otherwise. This coarse-grained data is then spatially filtered, for example convolved with a Gaussian kernel, such that coherent wavefronts of activation are present when the coarse-grained data is properly mapped for a given time bin.

A given window of this coarse-grained data, across some time period, is then used to determine the wavefront flow field. In order to find this flow field, we need a method to infer causality across time. In words, we must decide the direction along which each point on the wavefront moves between the current and next time step, allowing for the possibility of multiple different wavefronts at any given time. This would allow us to determine an instantaneous pseudo-velocity vector for each point along each wavefront. To achieve this with high accuracy and resolution, we utilize a method of local gradient matching to infer causality of the moving wavefronts.

In step 108, we first compute the spatial gradient of the activation maps for all times, such that we have the vector $[\partial_x\varphi_i(t), \partial_y\varphi_i(t)]$. At any given time step, we then define the direction of the instantaneous Wavefront Flow Vector (WFV) for each spatial point along the wavefront (points where $(\nabla\varphi_i)^2>0$) as:

$$WFV_i(t) \propto \vec{r}\left(i, \min_{R_{ij}<R^*}\{\|\nabla\varphi_i(t) - \nabla\varphi_j(t+1)\|\}\right).$$

In words, for each spatial point "i" along the wavefront we search all the points within a disk of radius R*, and find the spatial point "j" which shows the most similar gradient vector at time "t+1". We assume this represents a causal relationship between "i" and "j" and therefore that region "i" of the wavefront likely travels towards region "j" from time step "t" to time step "t+1". The magnitude of this vector can either be normalized to one or utilized to represent a dynamical quantity of interest such as the certainty of this causal relationship, conduction velocity, etc.

The vector field WFV is computed for all times "t" across our window and for all spatial points "i". Importantly, this is conducted both in forward time and in reverse time (where the resultant vector must be flipped for consistency). This allows us to detect rotational activity easier for both chirality of rotation, as wavefront curvature often favors the accuracy of either forward or reverse time $WFV_i$ determination for a given chirality. In step 110, once these individual $WFV_i$ have been computed for all times "t" in our window and all space points "i", they are then summed over this time window, including forward time and flipped vectors for reverse time for each spatial point "i", to get a vector field that we will call the Wavefront Flow Field, WFF. This WFF is a vector field which gives a picture of the net coherent flow field at each spatial point "i" across this particular time window. Any WFF vector at spatial location "i" which is below some threshold, resulting from inconsistent individual $WFV_i$ vectors, can be eliminated and either left blank or interpolated over.

From this vector field WFF, in step 112, we can then compute the local wavefront vorticity and divergence to determine the rotational and focal activity surrounding each spatial point "i" across a given time window. This is similar to taking the curl of WFF, with a weighting factor included in order to determine local vorticity around a spatial point. For each spatial point "i" we determine the unit vector field across our grid which is tangent everywhere to a circle centered at spatial point "i". Our vorticity is then the weighted sum of the dot product of this unit vector field and our WFF vector field. The weighting factor should have some decrease with spatial distance from point "i", such as a factor of inverse distance, in order to determine local vorticity accurately. The same process can be used to compute divergence by replacing the tangent unit vector field above with a unit vector field that is normal to a circle centered at spatial point "i". The resulting vorticity or divergence map can then also be convolved with a Gaussian kernel, or some other smoothing filter, in order to provide a clear map of rotational or focal intensity in step 114. In step 116, points with vorticity or divergence above a threshold value will be denoted and marked as likely rotor tips or focal sources, in the case of VF or AF signals, which may then be utilized by a treating physician to identify a desired location to apply treatment for the cardiac rhythm disorder, as noted in step 118.

For use in mapping heart rhythm signals in continuous time, the vector field WFF can be computed with a sliding window method across an entire episode. In particular, each WFF can be computed for some number of overlapping windows across an arrhythmic episode and interpolated in time to compute a time-dependent WFF. This time-dependent WFF could then be mapped on top of a phase map or activation map of wavefront propagation, and used to guide the eye to particular activation patterns across any episode of VF or AF. Most importantly, this method is entirely automated and therefore requires no manual input from the user, given a phase map or activation times.

Figure 2A:
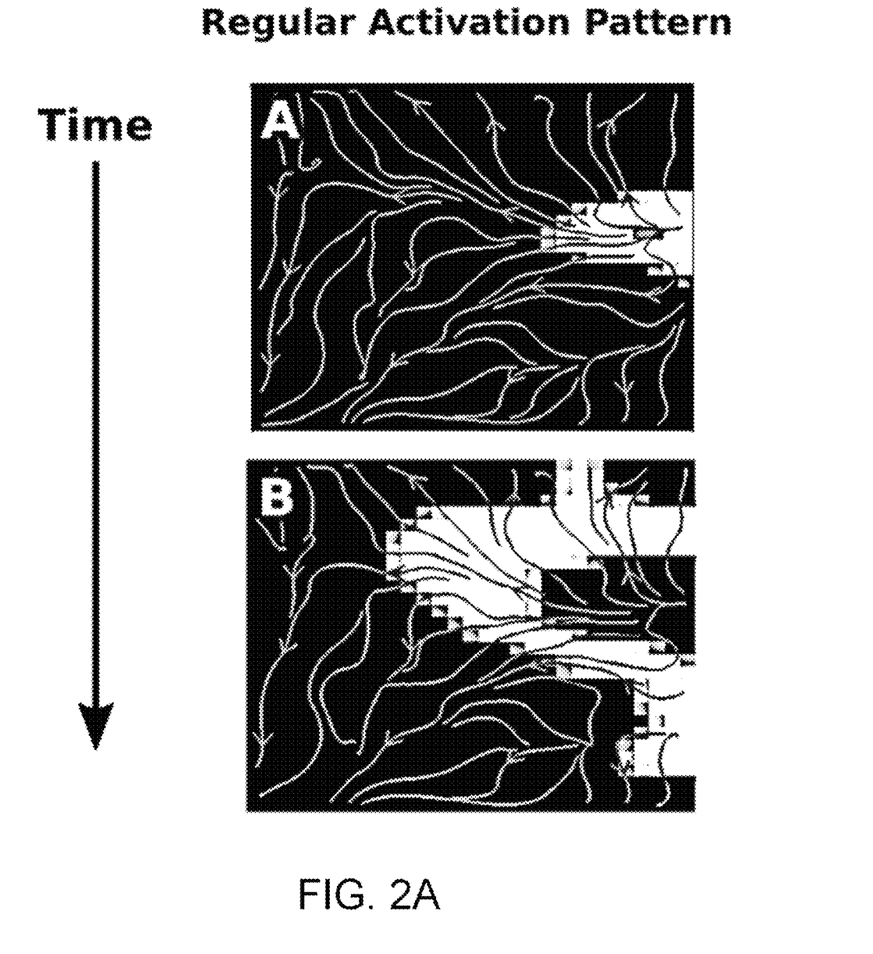
FIG. 2A is a pair of examples of activation maps for a regular activation pattern.
Figure 2B:
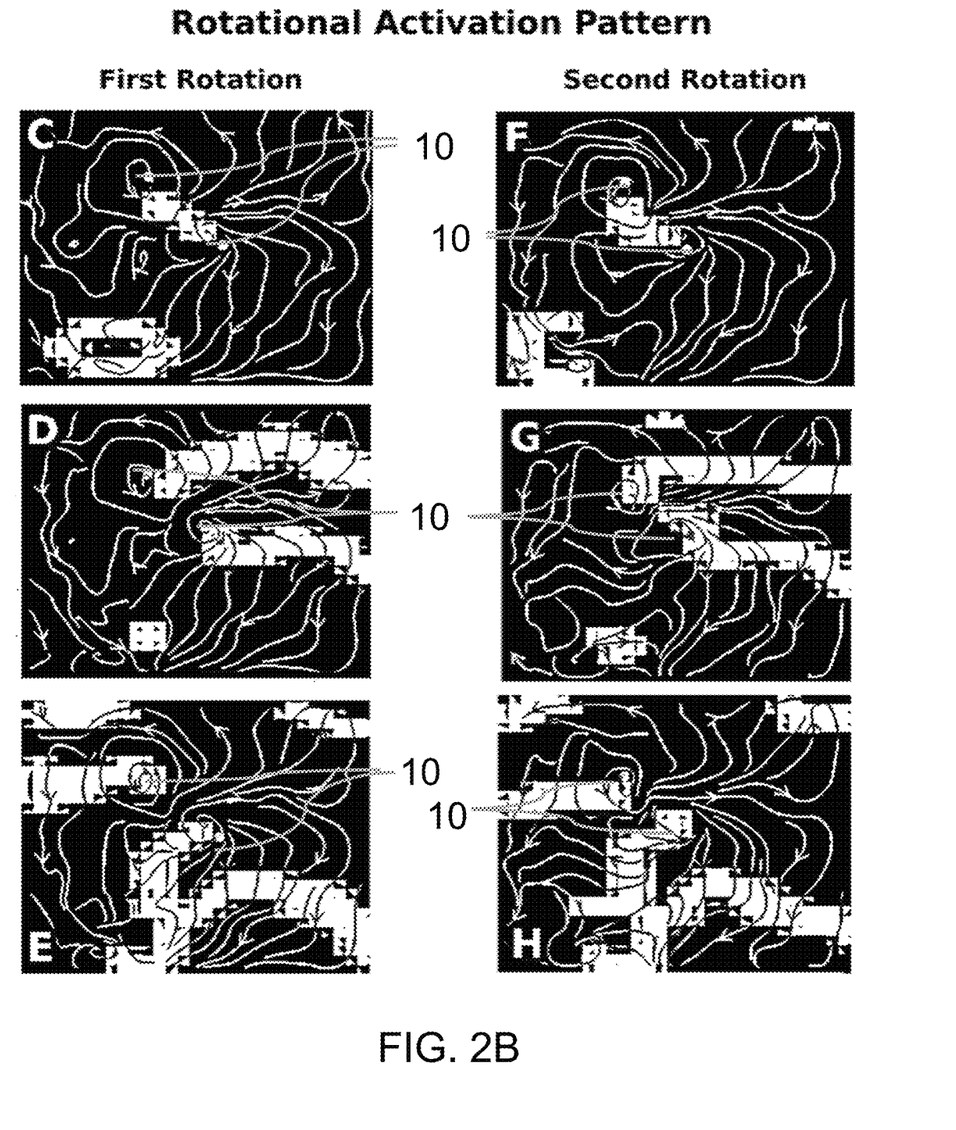
FIG. 2B provides examples of activation maps showing rotational activation in a first and second rotation.

FIG. 2A and FIG. 2B illustrate an example of a continuously updating implementation of this method for clinical activation time data from a patient experiencing VF. At the beginning of the episode, the activation dynamics were regular, as is seen in activation maps A and B of FIG. 2A (where white is activation and black is quiescent tissue). The flow field indicated by the curved lines (shown as white lines over a black background and black lines over a white background) is a streamline of the WFF at each instant, computed using an interpolated-sliding window method. It can be seen to track the motion as activation starts from a point and spreads across the tissue.

Halfway through the episode, two rotors appeared in a dual-reentry pattern, as shown in activation maps C-H of FIG. 2B. These activation maps show the rotors at subsequent times during reentry, with the WFF clearly outlining the complex multiple-rotor pathway. Furthermore, peaks in the maps of wavefront vorticity (values greater than some threshold) were computed for all times. These are shown as gray dots 10, and can be seen to pick out the rotor tips in maps C-H (FIG. 2B) whereas maps A and B (FIG. 2A) find no significant rotational activity.

Figure 2C:
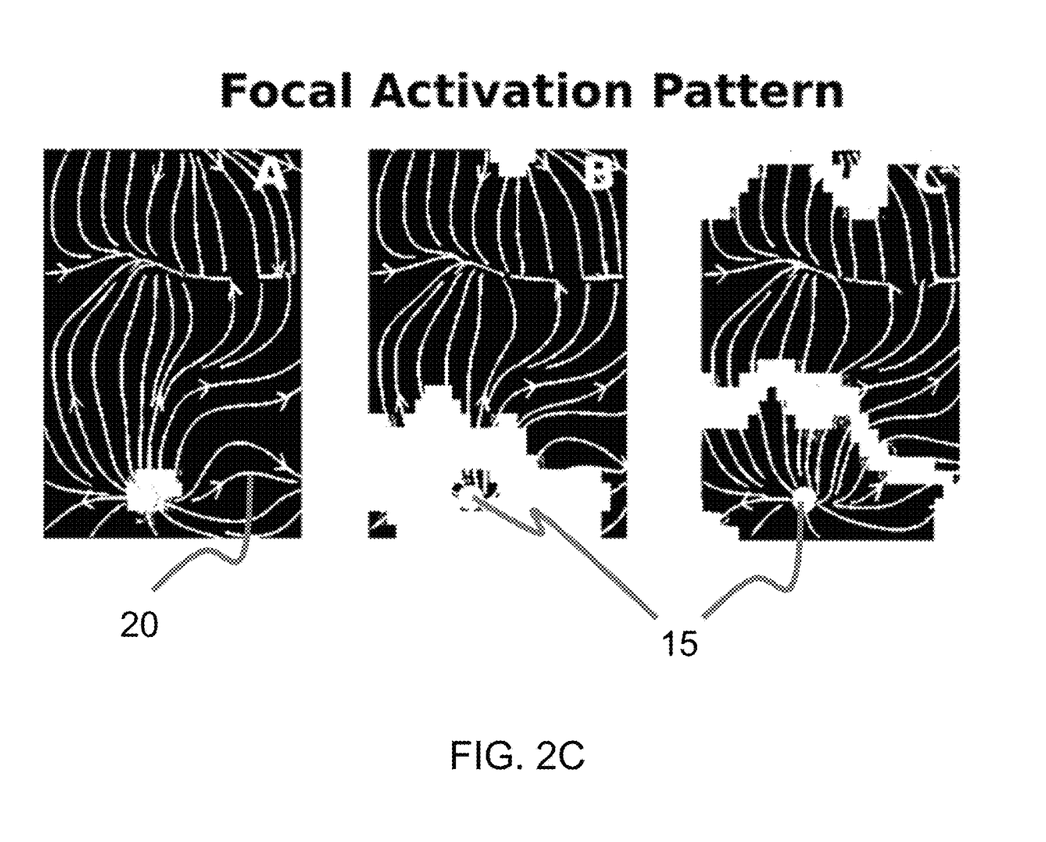
FIG. 2C illustrates examples of activation maps showing focal activation in a patient.

FIG. 2C illustrates an example of a detected focal source in a patient, according to one embodiment of the invention. The activation dynamics proceed from activation map A to activation map B and finally to activation map C, during which a focal source 15 is denoted based on the propagation of the activation (in white) and focal intensity emanating from the center point of activation. The flow field is indicated by curved lines 20, shown as white lines over a black background.

Exemplary System

Figures 3A, 3B:
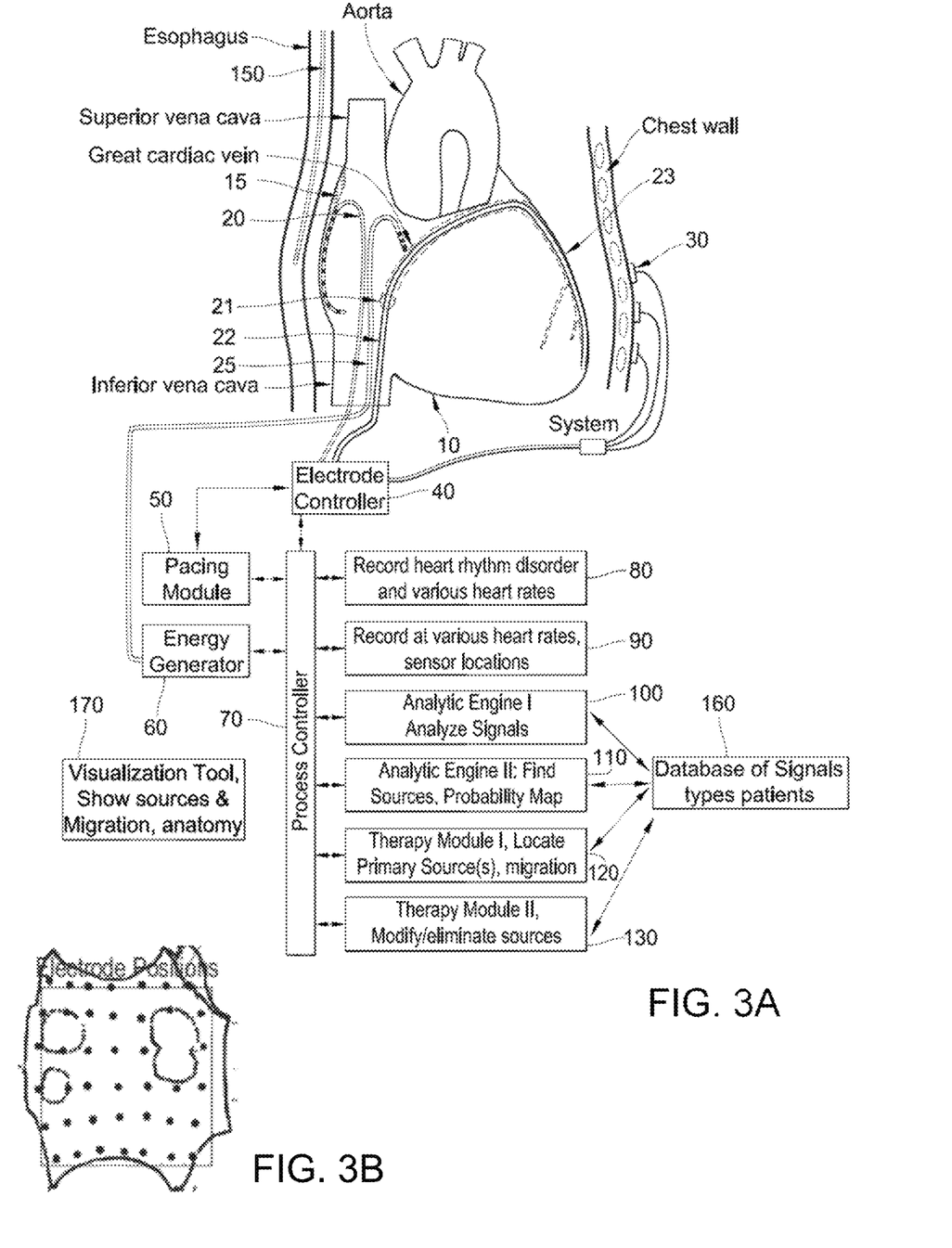
FIG. 3A is a schematic diagram of a system for use in embodiments of the invention.
FIG. 3B is a two-dimensional representation of a matrix of sensors shown as points or positions superimposed on a cardiac atrial surface.

FIG. 3A provides a schematic of various useful components (modules) that may be used in the process and system of the invention. The modules may be separate from each other and cooperatively interfaced to provide their function, or one or more of them may be integrated with each other of contained in the processor, such that the system has less separate hardware units. FIG. 3A depicts an embodiment which allows a cause of the disorder to be localized during a minimally invasive percutaneous procedure, or other procedures such as using surface ECG, a magnetocardiogram, an echocardiographic and/or Doppler measurements from ultrasound, electromagnetic radiation, sound waves, microwaves, or electrical impedance changes.

In FIG. 3A, electrical events in the heart 10 are recorded with sensing electrodes. These electrodes may be catheters 20 placed within the chambers or vasculature of the heart, including basket electrodes and custom-designed recording catheters. The electrodes may also be extensions of leads from an implanted pacemaker or cardioverter-defibrillator, catheters used to record monophasic action potentials or other signals that typically arrive via the vena cavae or coronary sinus 22.

FIG. 3B provides an example of a two-dimensional representation of a matrix or array of sensors shown as points or positions superimposed on a cardiac atrial surface, indicated by the irregular shape. The irregular shape represents the left atrium, cut horizontally through the plane of the mitral valve with the two halves folded up and down. This, the top portion of the shape corresponds to the superior mitral valve and the lower portion represents the inferior mitral value Electrodes 23 may record from the endocardial, epicardial or pericardial surface of the heart, accessed via electrodes 21 in the coronary sinus, via the electrodes 23 in the pericardial space or other routes. Electrodes may be located in proximity to the nerves supplying the heart 15, which may be located in the left atrium and ventricles. Electrodes may be virtual (computed) electrodes from a computerized mapping system, routine or high-resolution ECG mapping electrodes 30, electrodes implanted under or on the skin, or derived from methods to non-invasively detect signals without directly contacting the heart or body. Electrode information may also be derived from stored electrograms in a database 160.

An electrode 25 placed near the heart may be used to modify or destroy regions that are near or at the cause(s) for a rhythm disorder. If the electrode is an ablation catheter, it interfaces to an energy generator 60. Other electrodes may interface with a controller 40, and a pacing module 50, and all desirably communicate with a process controller 70. Ablation or pacing can be directed to nerves supplying the heart 15, which are located at many locations of the heart. Internal ablation electrodes may be replaced with an external ablation system, such as external probes during surgery, or as in external focused irradiation or photon beam as for cancer therapy. In addition, modification of sources, i.e., treatment of the causes of the disorder, may be achieved by delivering appropriate pharmaceutical compositions, gene therapy, cell therapy, or by excluding tissue (at surgery or by using specialized devices).

Process controller 70 may include various components or modules. On such component or module includes a sampling module 80 which is capable of recording signals during the rhythm disorder, recording at various rates not in the rhythm disorder (by pacing), and/or recording during rates that simulate the heart rhythm disorder (by pacing or other methods). Signal amplifiers (not shown) may be used to enhance the signal clarity and strength, and the process controller may also intelligently assign the fewest number of recording amplifiers to sense from a sufficient number of locations to identify and localize the cause. For instance, the system may use fifty to sixty physical amplifier channels to record from 128 sensors (for example, from two commercially available multipolar catheters), by recording those 128 sensors on a 'time-share' basis by time-slicing, or by activating individual/multiple sensors close to a rhythm cause while deactivating others. This 'switching' functionality may be performed by a switching component that connects the sensor device with the electronic control system, and that may be embodied in one or more other components. Switching may be manual or automatic, determined for instance on where causes of the heart rhythm disorder lie. Module 90 interfaces with the pacing module to provide additional heart rates for sensing the biosignal. This is particularly useful for the non-real time mode because it can study the heart at different heart rates even when not in the particular heart rhythm disorder being diagnosed and treated.

The inventive method and system processes the collected data using analytical methods, which may be performed by analytic modules. For example, in FIG. 3A, Module 100 is part I of an "Analytic Engine." This portion of the Analytic engine determines the onset and offset for the biologic signal over time, at each sensed location. This is implemented by creating a series of activation times (onset timing) and recovery times (offset timing) during the rhythm over time. The signal is typically represented as voltage over time (that is, as a voltage-time series). Activation time can be processed in many ways. The simplest includes manual assignment at each location. Automated or calculated assignment can be achieved by using zero of the first derivative to define maxima or minima, zero of the second derivative to indicate maximum upstroke or downstroke, or similar methods. Activation onset and offset times can also be assigned when the voltage time-series crosses a threshold. Another possible method to assign activation times is using pattern-matching. For example, a pattern selected to represent the activation duration can be correlated to the signal at multiple time points over time. The time when said correlation values are high indicate recurrences of said template, and thus are considered activation times. The template used for this analysis can also be obtained from stored data in a database, or computed from a rate estimate for the rhythm at that location. Simultaneous recordings from multiple sensors can help in analyzing activation, particularly for complex rhythms such as AF or VF when signal quality may be noisy, of poor quality or show multiple components at different times. From simultaneous recordings, a reference signal is selected, preferably at a nearby location to the channel being analyzed. Signals on the reference channel are used to select signal or signal components on the channel being analyzed. This can be done by using components that retain a similar timing over time, using pattern matching or correlation functions, vectorial analysis or other methods. If many methods are required, heuristics, pattern recognition methods and so-called 'fuzzy logic' approaches can be applied, constrained by known pathophysiology of the atrium.

Module 110 is part II of the Analytic Engine that actually computes and localizes, i.e., determines the existence and location of sources (causes) for the heart rhythm disorder.

Some embodiments of the invention include a "Therapy Engine," which may contain one of more modules designed to cooperatively perform different functions in the system and process. For example, module 120 in FIG. 3A may be responsible for determining the location and migration pattern of sources for the rhythm disorder within the heart. This may be a first module of the Therapy Engine, and is used to compute the location and spatial region which is required to be modified in order to treat or eliminate the rhythm disorder. Treatment may be by delivery of ablation energy or other means as discussed herein, and is not simply one point or region if the source migrates during ablation. Module 130 is representative of another module of the Therapy Engine, and desirably directly interfaces with the energy generator to ablate (destroy), modify (ablate or pace) or stimulate (pace) tissue at sites likely to represent sources. Alternatively, the Module 130 may be used to modify tissue without destructive energy, for example by delivering pharmaceutical agents, or gene or cellular therapies.

Module 170 of the system shown in FIG. 3A is representative of a tool to display the identification or location of causes visually or in auditory fashion, to assist the physician in treating or eliminating the rhythm disorder. For example, this module may include a display screen which permits the textual, graphic and/or auditory visualization on the screen of the rotor, focal or other cause of the disorder to be clearly seen by the practitioner. In some embodiments, a "movie" clip of the disorder found will be presented on the screen. This clip is a real-time presentation of the actual cause and location of the disorder. For example, once the analysis of the data has been performed in accordance with the process of the invention, i.e., the location of the signals and their activation onset times have been sequentially ordered, the result of this analysis and computation will be shown on the screen in the form of an activation trail. If the pattern of the activation trail signifies a series of activations revolving around a central core, then a rotor has been found and is in fact a cause of the disorder. Similarly, if the pattern of the activation trail signifies a series of activations which emanate radially from a central core region, then a focal beat has been found and is in fact a cause of the disorder. Thus, the inventive process permits the direct finding of the cause of the disorder and the convenient visualization of the existence, type and location of the disorder for the practitioner. In the event that no discernible pattern is found, i.e., the activation trail is not localized, then additional signal sampling by moving the sensor locations and/or turning-on already placed sensors may be appropriate. The additional signal samples may then be processed in accordance with the invention and shown on the screen. If a cause is found via the additional sampling and processing of the data, then a decision as to the appropriate treatment may be made. In the event that a dispersed activation trail and pattern is found, further additional sampling may be advisable until such time as the practitioner feels is sufficient. In some instances, the result of the process will render a finding of the existence and location of a rotor or a radially emanating focus. In other instances, where a dispersed pattern remains even after repeated sampling and processing, a diagnosis may be made ruling out a rotor or focal beats as the cause. Thus, the finding of a rotor or a focal point (beat) will be essentially a detection and diagnosis concurrently, whereas the lack of such a finding will be a diagnosis which may rule out the presence of either of these causes of the disorder.

Exemplary Computer-Implemented System

Figure 4:
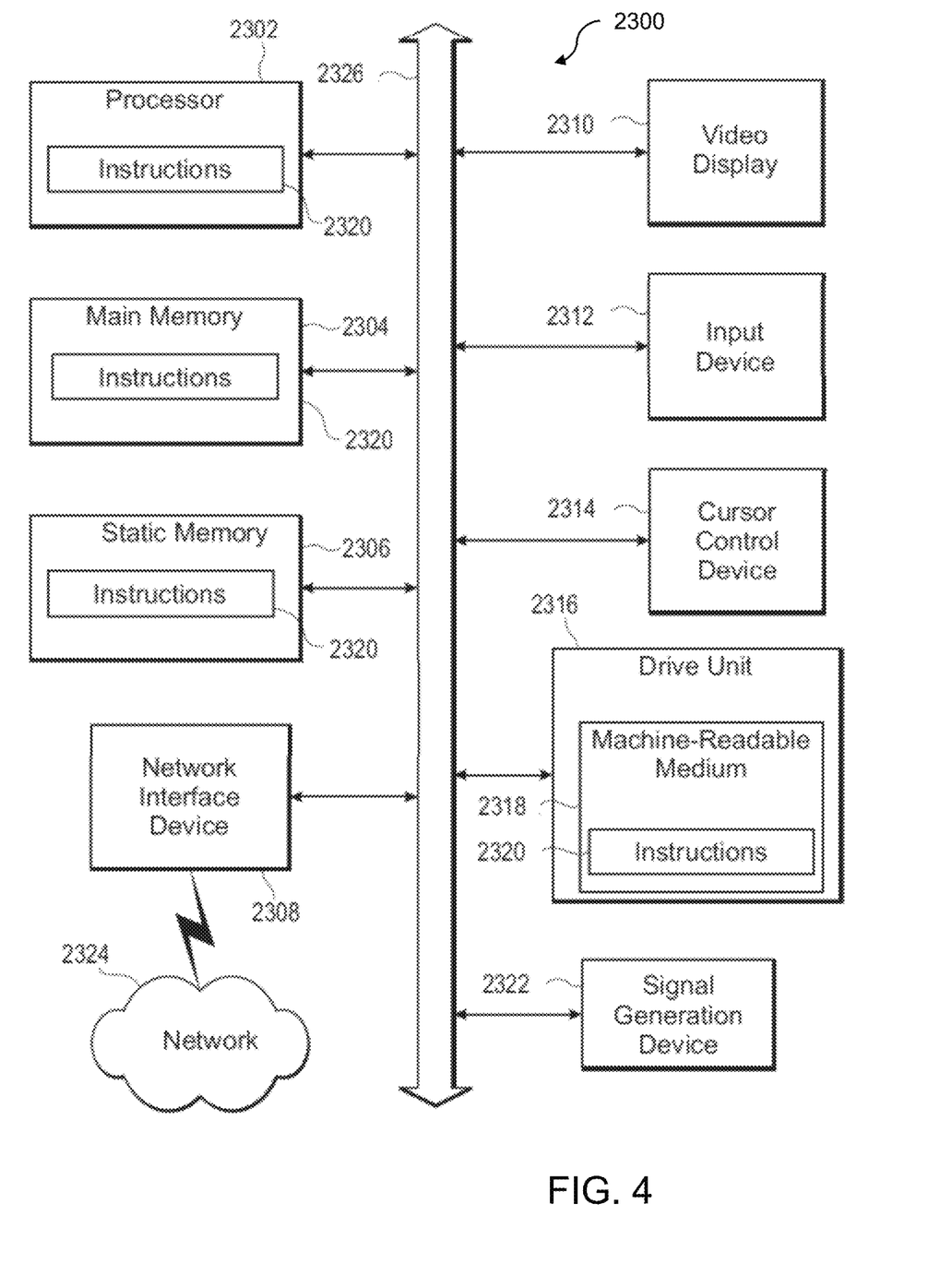
FIG. 4 is a block diagram of a computer system in accordance with the disclosed embodiments.

FIG. 4 is a block diagram of a computer system 2300. The computer system 2300 can include a set of instructions that can be executed to cause the computer system 2300 to perform the methods or computer-based functions disclosed herein. The computer system 2300 or any portion thereof, may operate as a standalone device or may be connected (e.g., using a network 2324) to other computer systems or devices disclosed herein. For example, the computer system 2300 can include or be included within any one or more of the catheter, computing device, server, biological sensor, and/or any other devices or systems disclosed herein.

In a networked deployment, the computer system 2300 may operate in the capacity of a server or a client machine in a server-client network environment, or a peer machine in a peer-to-peer (or distributed) network environment. The computer system 2300 can also be implemented as or incorporated into various devices, such as a personal computer (PC), a tablet PC, a personal digital assistant (PDA), a web appliance, a communications device, a mobile device, a server, client or any other machine capable of executing a set of instructions (sequential or otherwise) that specify actions to be taken by that machine. Further, while a single computer system 2300 is illustrated, the term "system" shall also be taken to include any collection of systems or sub-systems that individually or jointly execute a set, or multiple sets, of instructions to perform one or more computer functions.

The computer system 2300 can include a processor 2302, e.g., a central processing unit (CPU), a graphics-processing unit (GPU), or both. Moreover, the computer system 2300 can include a main memory 2304 and a static memory 2306 that can communicate with each other via a bus 2326. As shown, the computer system 2300 may further include a video display unit 2310, such as a liquid crystal display (LCD), a light emitting diode (LED), a flat panel display, a solid state display, or a cathode ray tube (CRT). Additionally, the computer system 2300 may include an input device 2312, such as a keyboard, and a cursor control device 2314, such as a mouse. The computer system 2300 can also include a disk drive unit 2316, a signal generation device 2322, such as a speaker or remote control, and a network interface device 2308.

In a particular embodiment, the disk drive unit 2316 may include a machine or computer-readable medium 2318 in which one or more sets of instructions 2320 (e.g., software) can be embedded. Further, the instructions 2320 may embody one or more of the methods, functions or logic as described herein. The instructions 2320 may reside completely, or at least partially, within the main memory 2304, the static memory 2306, and/or within the processor 2302 during execution by the computer system 2300. The main memory 2304 and the processor 2302 may also include computer-readable media.

In an alternative embodiment, dedicated hardware implementations, such as application specific integrated circuits, programmable logic arrays and other hardware devices, can be constructed to implement one or more of the methods, functions or logic described herein. Applications that may include the apparatus and systems of various embodiments can broadly include a variety of electronic and computer systems. One or more embodiments described herein may implement functions using two or more specific interconnected hardware modules or devices with related control and data signals that can be communicated between and through the modules, or as portions of an application-specific integrated circuit. Accordingly, the present system encompasses software, firmware, and hardware implementations.

The invention claimed is:

1. A method for analyzing complex cardiac activation patterns, comprising:
    collecting, via a computer processor, a plurality of cardiac signals at a plurality of locations corresponding to spatial locations of a patient's heart;
    determining activation times within the cardiac signals;
    binning the activation times according to a selected bin size;
    coarse-graining the binned activation times to generate coarse-grained data;
    determining at least one wavefront flow field (WFF) for a plurality of time windows using the coarse-grained data;
    computing a local wavefront vorticity using the at least one WFF to determine rotational activity surrounding each spatial location; and
    generating a vorticity map indicating likely rotational sources of complex cardiac activations.

2. The method of claim 1, wherein determining the activation times further comprises interpolating the activation times.

3. The method of claim 2, further comprising temporally smoothing the interpolated activation times by determining a time-averaged phase of a chosen time window.

4. The method of claim 1, wherein determining the wavefront flow field further comprises:
    determining a direction of movement of each point on a wavefront between a first time point and a second time point to define a wavefront flow vector ($WFV_i$) for all times and all spatial points across a given window of time; and
    summing the $WFV_i$ for all spatial points over all times in a given time window to generate the WFF for all spatial points for the given time window.

5. The method of claim 4, wherein the $WFV_i$ is defined in forward time and reverse time.

6. The method of claim 1, further comprising:
    computing a local wavefront divergence using the at least one WFF to determine focal activity surrounding each spatial location; and
    generating a divergence map indicating likely focal sources of complex cardiac activations.

7. The method of claim 6, wherein the step of generating a vorticity map or divergence map comprises convolving the vorticity map with a smoothing filter.

8. The method of claim 6, wherein likely rotational or focal sources of complex cardiac activations comprise points in the vorticity or divergence map exceeding a predetermined threshold.

9. A system for analyzing complex cardiac activation patterns, the system comprising:
    a computer processor programmed to execute the steps of:
        collecting, via a computer processor, a plurality of cardiac signals at a plurality of locations corresponding to spatial locations of a patient's heart;
        determining activation times within the cardiac signals;
        binning the activation times according to a selected bin size;
        coarse-graining the binned activation times to generate coarse-grained data;
        determining at least one wavefront flow field (WFF) for a plurality of time windows using the coarse-grained data;
        computing a local wavefront vorticity using the at least one WFF to determine rotational activity surrounding each spatial location; and
        generating a vorticity map indicating likely rotational sources of complex cardiac activations.

10. The system of claim 9, wherein determining the activation times further comprises interpolating the activation times.

11. The system of claim 10, further comprising temporally smoothing the interpolated activation times by determining a time-averaged phase of a chosen time window.

12. The system of claim 10, wherein determining the wavefront flow field further comprises:
   determining a direction of movement of each point on a wavefront between a first time point and a second time point to define a wavefront flow vector ($WFV_i$) for all times and all spatial points across a given window of time; and
   summing $WFV_i$ for all spatial points over all times in a given time window to generate the at least one WFF for all spatial points for the given time window.

13. The system of claim 12, wherein the $WFV_i$ is defined in forward time and reverse time.

14. The system of claim 9, further comprising:
   computing a local wavefront divergence using the at least one WFF to determine focal activity surrounding each spatial location; and
   generating a divergence map indicating likely focal sources of complex cardiac activations.

15. The system of claim 14, wherein the step of generating a vorticity map or divergence map comprises convolving the vorticity map with a smoothing filter.

16. The system of claim 9, wherein likely rotational or focal sources of complex cardiac activations comprise points in the vorticity map exceeding a predetermined threshold.

17. A method for analyzing complex cardiac activation patterns, comprising:
   collecting, via a computer processor, a plurality of cardiac signals at a plurality of locations corresponding to spatial locations of a patient's heart;
   determining activation times within the cardiac signals;
   binning the activation times according to a selected bin size;
   coarse-graining the binned activation times to generate coarse-grained data;
   determining at least one wavefront flow field (WFF) for a plurality of time windows using the coarse-grained data;
   computing a local wavefront divergence using the at least one WFF to determine focal activity surrounding each spatial location; and
   generating a divergence map indicating at least one likely focal source of complex cardiac activations.

18. The method of claim 17, wherein determining the wavefront flow field further comprises:
   determining a direction of movement of each point on a wavefront between a first time point and a second time point to define a wavefront flow vector ($WFV_i$) for all times and all spatial points across a given window of time; and
   summing the $WFV_i$ for all spatial points over all times in a given time window to generate the WFF for all spatial points for the given time window.

19. The method of claim 17, further comprising:
   computing a local wavefront vorticity using the at least one WFF to determine rotational activity surrounding each spatial location; and
   generating a vorticity map indicating at least one likely rotational source of the complex cardiac activations.

20. A method for analyzing complex cardiac activation patterns, comprising:
   collecting, via a computer processor, a plurality of cardiac signals at a plurality of locations corresponding to spatial locations of a patient's heart;
   determining activation times at the plurality of locations;
   computing a plurality of wavefront flow vectors within a selected time window for the spatial locations using local gradient matching;
   summing the plurality of wavefront flow vectors to define at least one wavefront flow field (WFF);
   using the at least one WFF, computing local wavefront vorticity to determine rotational activity associated with each spatial location or local wavefront divergence to determine focal activity associated with each spatial location; and
   generating one of a vorticity map indicating likely rotational sources of complex cardiac activations and a divergence map indicating likely focal sources of complex cardiac activations.

21. The method of claim 20, wherein the wavefront flow vectors are computed in both forward and reverse time, and wherein the vectors computed for reverse time are flipped.

22. The method of claim 20 wherein local wavefront vorticity is computed by:
   computing for each spatial point a unit vector field across a grid that is tangent everywhere to a circle centered at the spatial point; and
   computing a weighted sum of a dot product of the unit vector field and the WFF.

23. The method of claim 20 wherein local wavefront divergence is computed by:
   computing for each spatial point a unit vector field across a grid that is normal everywhere to a circle centered at the spatial point; and
   computing a weighted sum of a dot product of the unit vector field and the WFF.

* * * * *